(12) United States Patent
Schiene et al.

(10) Patent No.: US 10,813,890 B2
(45) Date of Patent: *Oct. 27, 2020

(54) PHARMACEUTICAL COMBINATION

(71) Applicant: Gruenenthal GmbH, Aachen (DE)

(72) Inventors: Klaus Schiene, Juechen (DE); Petra Bloms-Funke, Wuerselen (DE)

(73) Assignee: Grünenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/674,407

(22) Filed: Aug. 10, 2017

(65) Prior Publication Data

US 2017/0333369 A1  Nov. 23, 2017

Related U.S. Application Data

(63) Continuation of application No. 14/315,603, filed on Jun. 26, 2014, now abandoned, which is a continuation of application No. 13/159,845, filed on Jun. 14, 2011, now Pat. No. 8,846,765.

(60) Provisional application No. 61/354,835, filed on Jun. 15, 2010.

(30) Foreign Application Priority Data

Jun. 15, 2010 (EP) ..................................... 10006202

(51) Int. Cl.

| A61K 31/137 | (2006.01) |
|---|---|
| A61K 31/136 | (2006.01) |
| A61K 31/192 | (2006.01) |
| A61K 45/06 | (2006.01) |
| A61K 31/13 | (2006.01) |
| A61K 31/135 | (2006.01) |

(52) U.S. Cl.
CPC ............ *A61K 31/137* (2013.01); *A61K 31/13* (2013.01); *A61K 31/135* (2013.01); *A61K 31/136* (2013.01); *A61K 31/192* (2013.01); *A61K 45/06* (2013.01)

(58) Field of Classification Search
CPC .... A61K 31/136; A61K 31/192; A61K 31/13; A61K 31/135; A61K 31/137; A61K 45/06
See application file for complete search history.

(56) References Cited

U.S. PATENT DOCUMENTS

| 3,391,142 | A | 7/1968 | Mills et al. |
|---|---|---|---|
| 4,389,393 | A | 6/1983 | Schor et al. |
| 4,612,008 | A | 9/1986 | Wong et al. |
| 4,765,989 | A | 8/1988 | Wong et al. |
| 4,783,337 | A | 11/1988 | Wong et al. |
| 5,330,761 | A | 7/1994 | Baichwal |
| 5,399,362 | A | 3/1995 | Baichwal et al. |
| 5,455,046 | A | 10/1995 | Baichwal |
| 5,472,711 | A | 12/1995 | Baichwal |
| 6,248,737 | B1 | 6/2001 | Buschmann et al. |
| 6,248,789 | B1 | 6/2001 | Weg |
| 6,699,877 | B2* | 3/2004 | Gerlach ............... C07D 215/48 514/291 |
| 9,221,831 | B2 | 12/2015 | Kyle et al. |
| 2002/0010178 | A1 | 1/2002 | Buschmann et al. |
| 2004/0059003 | A1 | 3/2004 | Mermelstein et al. |
| 2005/0058706 | A1 | 3/2005 | Bartholomaeus et al. |
| 2007/0254960 | A1 | 11/2007 | Bloms-Funke et al. |
| 2008/0269326 | A1 | 10/2008 | Christoph et al. |
| 2009/0082466 | A1* | 3/2009 | Babul .................. A61K 9/4858 514/646 |
| 2009/0099138 | A1 | 4/2009 | Schiene et al. |
| 2009/0202634 | A1 | 8/2009 | Jans et al. |
| 2010/0190752 | A1 | 7/2010 | Schiene et al. |
| 2012/0225951 | A1 | 9/2012 | Christoph et al. |

FOREIGN PATENT DOCUMENTS

| DE | 44 26 245 A1 | 2/1996 |
|---|---|---|
| JP | 2002-506047 A | 2/2002 |
| JP | 2002-520363 A | 7/2002 |
| JP | 2003-201254 A | 7/2003 |
| JP | 2006-500395 A | 1/2006 |
| JP | 2009-539792 A | 11/2009 |
| WO | WO 99/45963 A1 | 9/1999 |
| WO | WO 00/03716 A1 | 1/2000 |
| WO | 01 76576 A2 | 10/2001 |
| WO | WO 03/053427 A1 | 7/2003 |

(Continued)

OTHER PUBLICATIONS

Jamero, Pain Management, 2011 (Year: 2011).*
Larsen, Open J of Dentistry and Oral Medicine, 5(4), 59-71, 2017 (Year: 2017).*
Ma et al., Editor: Sirinathsinghji, NMDA Antagonists as Potential Analgesic Drugs, 2002 (Year: 2002).*
Newport, Am J Psychiatry, 2015, p. 950-966 (Year: 2015).*
Paoletti et al., Neuroscience, 14, Jun. 2013 (Year: 2013).*
Vyklicky, (Physiol Res 63, S191-S203, 2014). (Year: 2014).*
Svensson, J Neural Transm, 1991, 117-129 (Year: 1991).*
Albensi (Am J of Alzheimer's Disease and Other Dementias, 19, 5, 2004). (Year: 2004).*
Newport, Am J Psychiatry, 2015, 950-966 (Year: 2015).*
PCT/ISA/237 Form (Four (4) pages), 2010.
International Search Report dated Sep. 13, 2011 (Five (5) pages).
H. Buschmann et al., "7.2 NMDA Receptor Antagonists", 2002, pp. 389-428.

(Continued)

*Primary Examiner* — Umamaheswari Ramachandran
(74) *Attorney, Agent, or Firm* — Norris McLaughlin, P.A.

(57) ABSTRACT

A pharmaceutical combination comprising as components (a) at least one 3-(3-dimethylamino-1-ethyl-2-methyl-propyl)-phenol compound, and (b) at least one NMDA-antagonist, a pharmaceutical formulation and a dosage form comprising such a combination, and a method of treating pain, e.g. inflammatory pain or neuropathic pain, in which components (a) and (b) are administered simultaneously or sequentially to a mammal, with component (a) being administered either before or after component (b), and with components (a) or (b) being administered to the mammal either via the same pathway of administration or via different pathways of administration.

16 Claims, No Drawings

(56) References Cited

FOREIGN PATENT DOCUMENTS

| WO | WO 2004/022002 A2 | 3/2004 |
|---|---|---|
| WO | WO 2007/128412 A1 | 11/2007 |
| WO | WO 2007/128413 A1 | 11/2007 |
| WO | WO 2007/141018 A1 | 12/2007 |
| WO | 2008 023261 A1 | 2/2008 |
| WO | WO 2009/067703 A2 | 5/2009 |
| WO | WO 2009/094563 A2 | 7/2009 |
| WO | WO 2009/094563 A3 | 7/2009 |
| WO | WO 2010/025931 A2 | 3/2010 |
| WO | WO 2010/025931 A3 | 3/2010 |
| WO | 2011 157391 A1 | 12/2011 |
| WO | 2012 085656 A2 | 6/2012 |
| WO | 2013 156850 A1 | 10/2013 |

OTHER PUBLICATIONS

Claus S. Larsen et al., "Design and Application of Prodrugs", 2002, pp. 410-458.

Lowell O. Randall et al,. "A Method for Measurement of Analgesic Activity on Inflamed Tissue", Department of Pharmacology Hoffmann-La Roch, Inc. Nutley 10, vol. 157, pp. 409-419, 1957.

Ronald J. Tallarida et al., "Statistical Analysis of Drug-Drug and Site-Site Interactions with Isobolograms", Life Sciences, vol. 45, 1989, Pergamon Press, pp. 947-961, USA.

T. Patrick Harty et al., "Felbamate block of recombinant N-methyl-D-aspartate receptors: selectivity for the NR2B subunit", Epilepsy Research, vol. 39, 2000, pp. 47-55.

Maryandele J. O'Neil et al., The Merck Index, 14$^{th}$ Edition, 2006, (six (6) pages).

Ravin, L. PhD., "Preformulation", Remington Chapter 76, pp. 1409-1423, 1985 (Fifteen (15) pages).

Disanto, A., "Bioavailability and Bioequivalency Testing", Remington Chapter 77, pp. 1424-1431, 1985 (Eight (8) pages).

Knevel, A. PhD., "Separation", Remington Chapter 78, pp. 1432-1442, 1985 (Eleven (11) pages).

Phillips, G Briggs, Ph.D., "Sterilization", Remington Chapter 79, pp. 1443-1454, 1985 (Twelve (12) pages).

Siegel, F. PhD., "Tonicity, Osmoticity, Osmolality and Osmolarity", Remington Chapter 80, pp. 1455-1472, 1985 (Eighteen (18) pages).

Giles et al., "Plastic Packaging Materials", Remington Chapter 81, pp. 1473-1477, 1985 (Five (5) pages).

Lintner, C. PhD., "Stability of Pharmaceutical Products", Remington Chapter 82, pp. 1478-1486, 1985 (Nine (9) pages).

Erskine, C., Jr., "Quality Assurance and Control" Remington Chapter 83, pp. 1487-1491, 1985 (Five (5) pages).

Nairn, J.G. Ph.D., "Solutions, Emulsions, Suspensions and Extractives", Remington Chapter 84, pp. 1492-1517, 1985 (Twenty-six (26) pages).

Avis, K. DSc., "Parenteral Preparations", Remington Chapter 85, pp. 1518-1541, 1985 (Twenty-four (24) pages).

Turco et al., "Intravenous Admixtures", Remington Chapter 86, pp. 1542-1552, 1985 (Eleven (11) pages).

Mullins, J. PhD., "Ophthalmic Preparations", Remington Chapter 87, pp. 1553-1566, 1985 (Fourteen (14) pages).

Block, L. PhD., "Medicated Applications", Remington Chapter 88, pp. 1567-1584, 1985 (Eighteen (18) pages).

Rippie, E. PhD., "Powders", Remington Chapter 89, pp. 1585-1602, 1985 (Eighteen (18) pages).

King et al., "Oral Solid Dosage Forms", Remington Chapter 90, pp. 1603-1632, 1985 (Thirty (30) pages).

Porter, S. PhD., "Coating of Pharmaceutical Dosage Forms", Remington Chapter 91, pp. 1633-1643, 1985 (Eleven (11) pages).

Longer et al., "Sustained-Release Drug Delivery Systems", Remington Chapter 92, pp. 1644-1661, 1985 (Eighteen (18) pages).

Sclarra et al., "Aerosols", Remington Chapter 93, pp. 1662-1677, 1985 (Sixteen (16) pages).

Ketalar for Intravenous Injection, 2010, Daiichi Sankyo Company, Ketamine HCI package insert (Three (3) pages).

Japanese-language Reexamination Report issued in counterpart Japanese Application No. 2013-514579 dated Jun. 8, 2016 with English translation (Four (4) pages).

H. Frey et al., "Effect of Psychotropic Agents on a Model of Absence Epilepsy in Rats," Neuropharmacology, 1991, pp. 651-656, vol. 30, No. 6.

M. Rogawski, "The NMDA Receptor, NMDA Antagonists and Epilepsy Therapy," Drugs, 1992, pp. 279-292, vol. 44, No. 3.

C. Parsons et al., "Memantine is a clinically well tolerated N-methyl-D-aspartate (NMDA) receptor antagonist—a review of preclinical data," Neuropharmacology, 1999, pp. 735-767, vol. 38.

Partial English-language translation of Japanese Office Action issued in counterpart Japanese Application No. 2015-151003 dated Jul. 27, 2016 (one (1) page).

A. B. Petrenko et al., "The Role of N-Methyl-D-Aspartate (NMDA) Receptors in Pain: A Review," Anesth. Analg., 2003, pp. 1108-1116, vol. 97, the International Anesthesia Research Society.

JP 2003201254A—English translation, 2003.

Alekseev , "Optical isomerism and the pharmacological activity of drugs"; Sorosovsky Obrazovatel'NY , Journal No. 1, 1998.

Russian-Language Office Action issued in counterpart Russian Application No. 2016119041/15(029881) dated Aug. 28, 2017 with English translation (15 pages).

Kharkevich, "Pharmacology", Third Edition, 1987, p. 51, Moscow Meditsina with English translation (5 pages).

\* cited by examiner

PHARMACEUTICAL COMBINATION

CROSS REFERENCE TO RELATED APPLICATIONS

This application is a continuation of U.S. patent application Ser. No. 14/315,603, filed Jun. 26, 2014, which is a continuation of U.S. patent application Ser. No. 13/159,845, filed Jun. 14, 2011, which claims benefit of provisional patent application Ser. No. 61/354,835 and European patent application no. EP 10 006 202.5, both filed Jun. 15, 2010 and incorporated herein by reference.

BACKGROUND OF THE INVENTION

The present invention relates to a combination comprising as components (a) at least one 3-(3-dimethylamino-1-ethyl-2-methyl-propyl)-phenol compound, and (b) at least one N-methyl-D-aspartate antagonist (NMDA-antagonist), a pharmaceutical formulation and a dosage form comprising said combination as well as a method of treating pain, e.g. inflammatory pain or neuropathic pain, wherein components (a) and (b) are administered simultaneously or sequentially to a mammal, whereby component (a) may be administered before or after component (b) and whereby components (a) or (b) are administered to the mammal either via the same or a different pathway of administration.

The treatment of chronic and acute pain conditions is extremely important in medicine. There is currently a worldwide demand for additional, not exclusively opioid-based, but highly effective pain treatment. The urgent need for action for patient-oriented and purposeful treatment of pain conditions, this being taken to mean the successful and satisfactory treatment of pain for the patient, is documented in the large number of scientific papers that have recently appeared in the field of applied analgesics and fundamental research work on nociception.

Even if the analgesics that are currently used for treating pain, for example opioids, NA- and 5HT-reuptake inhibitors, NSAIDS and COX inhibitors, are analgesically effective, side effects nevertheless sometimes occur. Sometimes substance combinations comprising two different drugs show super-additive therapeutic effects upon administration. Due to such a super-additive effect the overall dose and accordingly the risk of undesired side effects can be reduced. Examples of combinations comprising 3-(3-dimethylamino-1-ethyl-2-methyl-propyl)-phenol are disclosed in US 2009/099138 (=WO 2007/128412), US 2007/254960 (=WO 2007/128413) and US 2010/190752 (=WO 2010/025931).

SUMMARY OF THE INVENTION

Thus, it was an object of the present invention to provide further combinations having improved properties.

It was also an object of the present invention to find further combinations that are suitable for the treatment of pain and that preferably exhibit fewer undesired side effects compared to its individual components, if administered in effective doses.

It has been found that a combination comprising (a) at least one 3-(3-dimethylamino-1-ethyl-2-methyl-propyl)-phenol compound, and (b) at least one NMDA-antagonist exhibits an analgesic effect. If these components are present in the composition in such a weight ratio that a super-additive or synergistic therapeutic effect is observed upon administration to the patients, the overall administered dose may be lowered, so that fewer undesired side-effects will occur.

Accordingly, the present invention relates to a pharmaceutical combination comprising as components
(a) 3-(3-dimethylamino-1-ethyl-2-methyl-propyl)-phenol of formula (I)

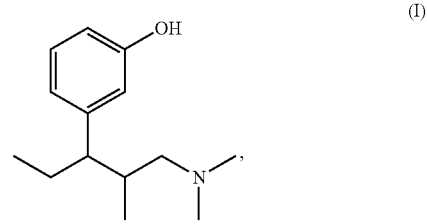 [SMILES: CCC(c1cccc(O)c1)C(C)CN(C)C]

optionally in form of one of its pure stereoisomers, in particular an enantiomer or a diastereomer, a racemate or in form of a mixture of its stereoisomers, in particular enantiomers and/or diastereomers in any mixing ratio, or any corresponding acid addition salt thereof, and
(b) at least one NMDA-antagonist.

In one embodiment of the pharmaceutical combination according to the invention, the compound of formula (I) is selected from
(1R,2R)-3-(3-dimethylamino-1-ethyl-2-methyl-propyl)-phenol,
(1S,2S)-3-(3-dimethylamino-1-ethyl-2-methyl-propyl)-phenol,
(1R,2S)-3-(3-dimethylamino-1-ethyl-2-methyl-propyl)-phenol,
(1S,2R)-3-(3-dimethylamino-1-ethyl-2-methyl-propyl)-phenol, and any mixture thereof.

In another embodiment of the pharmaceutical combination of the invention, the compound of formula (I) is selected from
(1R,2R)-3-(3-dimethylamino-1-ethyl-2-methyl-propyl)-phenol, and
(1S,2S)-3-(3-dimethylamino-1-ethyl-2-methyl-propyl)-phenol, and any mixture thereof.

In yet another embodiment, the pharmaceutical combination of the invention comprises
(a) the compound (1R,2R)-3-(3-dimethylamino-1-ethyl-2-methyl-propyl)-phenol of formula (I'),

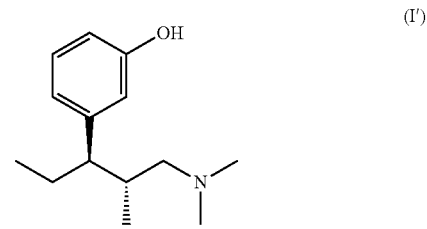 [SMILES: CC[C@@H](c1cccc(O)c1)[C@@H](C)CN(C)C]

or an acid addition salt thereof, and
(b) at least one NMDA-antagonist.

The compound 3-(3-dimethylamino-1-ethyl-2-methyl-propyl)-phenol of formula (I), its stereoisomers and corresponding salts thereof as well as methods for their preparation are well known, for example, from U.S. Pat. No. 6,248,737, the entire disclosure of which is incorporated herein by reference.

The definition of component (a) as used herein includes 3-(3-dimethylamino-1-ethyl-2-methyl-propyl)-phenol, derivatives thereof and stereoisomers thereof in any possible form, thereby particularly including solvates and polymorphs, salts, in particular acid addition salts and corresponding solvates and polymorphs.

The term derivative as used herein particularly includes prodrugs such as ethers and esters of the active substance. Suitable methods for selecting and preparing a pro-drug of a given substance are for example described in "*Textbook of Drug Design and Discovery*", 3$^{rd}$ edition, 2002, chapter 14, pages 410-458, Editors: Krogsgaard-Larsen et al., Taylor and Francis. The respective parts of said literature description are incorporated by reference and form part of the present disclosure.

If component (a) is present as mixture of enantiomers, such a mixture may contain the enantiomers in racemic or non-racemic form. A non-racemic form could, for example, contain the enantiomers in a ratio of 60±5:40±5, 70±5:30±5, 80±5:20±5 or 90±5:10±5.

The compound 3-(3-dimethylamino-1-ethyl-2-methyl-propyl)-phenol and its stereoisomers according to component (a) may be present in the pharmaceutical composition of the present invention in form of an acid addition salt, whereby any suitable acid capable of forming such an addition salt may be used.

The conversion of 3-(3-dimethylamino-1-ethyl-2-methyl-propyl)-phenol into a corresponding addition salt, for example, via reaction with a suitable acid may be effected in a manner well known to persons skilled in the art. Suitable acids include, but are not limited to, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. Salt formation is preferably effected in a solvent, for example, diethyl ether, diisopropyl ether, alkyl acetates, acetone and/or 2-butanone. Moreover, trimethylchlorosilane in aqueous solution is also suitable for the preparation of hydrochlorides.

The NMDA receptor is part of a glutamatergic neurotransmitter-receptor system, the so-called NMDA-receptor/ion-channel complex. It comprises different binding sites that are located inside and outside of the ion-channel. An NMDA receptor antagonist or simply NMDA-antagonist is a substance that interacts with such a binding site and exerts at least partially inhibiting properties related to said binding site.

NMDA-antagonists are well known to those skilled in the art and particularly include, without being limited thereto, N-containing phosphonic acids, such as norvaline (AP5), D-norvaline (D-AP5), 4-(3-phosphono-propyl)-piperazine-2-carboxylic acid (CPP), D-(E)-4-(3-phosphonoprop-2-enyl)piperazine-2-carboxylic acid (D-CPPene), cis-4-(phosphonomethyl)-2-piperidine carboxylic acid (Selfotel, CGS 19755), SDZ-220581, PD-134705, LY-274614 and WAY-126090; quinolinic acids, such as kynurenic acid, 7-chloro-kynurenic acid, 7-chloro-thiokynurenic acid and 5,7-dichloro-knynurenic acid, prodrugs thereof, such as 4-chlorokynurenine and 3-hydroxy-kynurenine; 4-am ino-tetrahydrochinolin-carboxylates, such as L-689,560; 4-hydroxyquinolin-2(1H)-ones, such as L-701,324; quinoxalin-ediones, such as licostinel (ACEA-1021) and CGP-68, 730A; 4,6-dichloro-indole-2-carboxylate derivatives such as MDL-105,519, gavestinel (GV-150,526) and GV-196,771A; tricyclic compounds, such as ZD-9,379 and MRZ-2/576, (+)-HA-966, morphinan derivatives such as dextromethorphan and dextrophan; benzomorphans, such as BIII-277CL; other opioids, such as dextropropoxyphene, ketobemidone, dextromethadone and D-morphine; amino-adamantanes, such as amantadine and memantine; amino-alkyl-cyclohexanes, such as MRZ-2/579; ifenprodil and ifenprodile-like compounds such as eliprodil and PD-196,860; iminopyrimidines; or other NMDA-antagonists such as nitroprusside, D-cycloserine, 1-am inocyclopropane-carboxylic acid, dizocilpine (MK 801) and its analogs, phencyclidine (PCP), ketamine ((R,S)-2-(2-Chlorphenyl)-2-(methylam ino)cyclo-hexan-1-on), (R)-ketamine, (S)-ketamine, remacem ide and its des-glycinyl-metabolite FPL-12,495, AR-R-15,896, methadone, sulfazocine, AN19/AVex-144, AN2/AVex-73, Besonprodil, CGX-1007, EAB-318, Felbamate and NPS-1407. NMDA-Antagonists are, for example, disclosed in "Analgesics," edited by H. Buschmann, T. Christoph, E. Friderichs, C. Maul, B. Sundermann, 2002, Wiley-VCH Verlag GmbH & Co. KGaA, Weinheim, Germany, in particular pages 389-428. The respective parts of the description are hereby incorporated by reference and form part of the present disclosure.

Some NMDA-antagonists such as ketamine and memantine are known to be useful in the treatment of neuropathic pain. In one embodiment of the present invention one or more of these NMDA-antagonists is used as component (b).

Also included are stereoisomers, salts, solvates, polymorphs and derivatives of the NMDA-antagonist component as well as mixtures of any of the foregoing.

In another embodiment of the pharmaceutical combination of the invention, the NMDA-antagonist according to component (b) is memantine or an acid addition salt thereof such as the hydrochloride addition salt.

In a further embodiment of the pharmaceutical combination of the invention, the NMDA-antagonist according to component (b) is ketamine or an acid addition salt thereof such as the hydrochloride addition salt.

In yet another embodiment of the pharmaceutical combination of the invention, the NMDA-antagonist according to component (b) is (R,S)-ketamine or an acid addition salt thereof such as the hydrochloride addition salt.

In still another embodiment of the pharmaceutical combination of the invention, the NMDA-antagonist according to component (b) is (S)-ketamine or an acid addition salt thereof such as the hydrochloride addition salt.

Another specific embodiment of the present invention is a combination comprising (a) (1R,2R)-3-(3-dimethylamino-1-ethyl-2-methyl-propyl)-phenol, or an acid addition salt thereof such as the hydrochloride addition salt, and (b) memantine or an acid addition salt thereof such as the hydrochloride addition salt.

Yet another specific embodiment of the present invention is a combination comprising (a) (1R,2R)-3-(3-dimethyl-amino-1-ethyl-2-methyl-propyl)-phenol, or an acid addition salt thereof such as the hydrochloride addition salt, and (b) ketamine or an acid addition salt thereof such as the hydrochloride addition salt.

Yet a further specific embodiment of the present invention is a combination comprising (a) (1R,2R)-3-(3-dimethyl-amino-1-ethyl-2-methyl-propyl)-phenol, or an acid addition salt thereof such as the hydrochloride addition salt, and (b) (R,S)-ketamine or an acid addition salt thereof such as the hydrochloride addition salt.

Yet still another specific embodiment of the present invention is a combination comprising (a) (1R,2R)-3-(3-dimethylamino-1-ethyl-2-methyl-propyl)-phenol, or an acid addition salt thereof such as the hydrochloride addition salt, and (b) (S)-ketamine or an acid addition salt thereof such as the hydrochloride addition salt.

Some NMDA-antagonists comprise functional groups, for example, acidic groups such as carboxy groups which are capable of forming salts with the 3-(3-dimethylamino-1-ethyl-2-methyl-propyl)-phenol component of formula (I), thereby incorporating both components (a) and (b) in one and the same salt.

Thus, in another embodiment of the present invention the pharmaceutical combination of the invention comprises components (a) and (b) in form of a salt formed from these two components. Such a salt formation may be partial, i.e. the composition of the invention comprises one or both of these components also in their non-salt form, or the salt formation may essentially be complete.

Both components (a) and (b) as part of the pharmaceutical combination of the invention may be administered in amounts up to their maximum daily dosage, which is known to persons skilled in the art.

Memantine may preferably be administered to a patient in a daily dosage of 1 to 20 mg.

Racemic ketamine may preferably be administered to a patient in a daily dosage of 0.1 to 10 mg/kg, and the S-enantiomer of ketamine may preferably be administered to a patient in a daily dosage of 1 to 10 mg/kg.

The compound (1R,2R)-3-(3-dimethylamino-1-ethyl-2-methyl-propyl)-phenol may preferably be administered to a patient in a daily dosage of 25 to 1000 mg, particularly preferably in a dosage of 50 to 800 mg, more particularly preferably in a dosage of 100 to 600 mg.

When administered as part of the combination according to the present invention, the administered amount per day of component (a) and/or component (b) may be less than the respective maximum daily dosage and be, for example, 75±15 wt.-%, 75±10 wt.-%, 75±5 wt.-%, 50±15 wt.-%, 50±10 wt.-%, 50±5 wt.-%, 25±15 wt.-%, 25±10 wt.-% and 25±5 wt.-% for each of the components.

In another embodiment of the present invention the pharmaceutical combination of the invention may contain components (a) and (b) essentially in an equieffective ratio.

In yet a further embodiment of the combination according to the invention, components (a) and (b) are present in such a weight ratio that the resulting composition will exert a supra-additive or synergistic effect upon administration to a patient. Suitable weight ratios can be determined by methods well known to those skilled in the art.

Both components (a) and (b) may also be present in the pharmaceutical combination of the invention in ratios deviating from the equieffective ratio. For, example, each of the components could be present in a range from 1/50 of the equieffective amount to 50 times the equieffective amount, from 1/20 of the equieffective amount to 20 times the equieffective amount, from 1/10 of the equieffective amount to 10 times the equieffective amount, from 1/5 of the equieffective amount to 5 times the equieffective amount, from 1/4 of the equieffective amount to 4 times the equieffective amount, from 1/3 of the equieffective amount to 3 times the equieffective amount, or from 1/2 of the equieffective amount to 2 times the equieffective amount.

In another embodiment of the present invention the components (a) and (b) can be administered in a specific dosage regimen to treat pain, for example, neuropathic pain. Components (a) and (b) may be administered simultaneously or sequentially one after another, in each case via the same or different administration pathways.

Another aspect of the present invention is therefore a method of treating pain, characterized in that components (a) and (b) are administered simultaneously or sequentially to a mammal, wherein component (a) may be administered before or after component (b), and wherein components (a) or (b) are administered to the mammal either via the same or a different pathway of administration.

The term pain as used herein includes but is not limited to inflammatory pain, neuropathic pain, acute pain, chronic pain, visceral pain, migraine pain and cancer pain.

Suitable pathways of administration include, but are not limited to, oral, intravenous, intraarterial, intraperitoneal, intradermal, transdermal, intrathecal, intramuscular, intranasal, transmucosal, subcutaneous, and rectal administration.

The combinations according to the invention are toxicologically safe and are therefore suitable for the treatment of mammals, particularly humans including infants, children and adults.

Thus, in a further aspect the present invention relates to a pharmaceutical composition comprising a pharmaceutical combination according to the invention as described herein and one or more auxiliary agents.

In a further aspect the present invention relates to a pharmaceutical dosage form comprising a pharmaceutical combination of the invention as described herein and one or more auxiliary agents.

In one embodiment, the pharmaceutical dosage form of the invention is suitable for being administered orally, intravenously, intraarterially, intraperitoneally, intradermally, transdermally, intrathekally, intramuscularly, intranasally, transmucosally, subcutaneously, or rectally.

The formulations and dosage forms of the invention may contain auxiliary agents, for example, carriers, fillers, solvents, diluents, colorants and/or binders. The selection of auxiliary agents and of the amounts of the same to be used depends, for example, on how the drug is to be administered, e.g. orally, intravenously, intraarterially, intraperitoneally, intradermally, transdermally, intramuscularly, intranasally or locally, for example for infections of the skin, of the mucous membranes or of the eye.

Suitable auxiliary agents in the context of this invention include, in particular, any substances known to persons skilled in the art to be useful for the preparation of galenical formulations. Examples of suitable auxiliary agents include, but are not limited to, water, ethanol, 2-propanol, glycerol, ethylene glycol, propylene glycol, polyethylene glycol, polypropylene glycol, glucose, fructose, lactose, saccharose, dextrose, molasses, starch, modified starch, gelatine, sorbitol, inositol, mannitol, microcrystalline cellulose, methyl cellulose, carboxymethyl cellulose, cellulose acetate, shellac, cetyl alcohol, polyvinyl pyrrolidone, paraffins, waxes, natural and synthetic gums, acacia gum, alginates, dextran, saturated and unsaturated fatty acids, stearic acid, magnesium stearate, zinc stearate, glycerol stearate, sodium lauryl sulphate, edible oils, sesame oil, coconut oil, peanut oil, soybean oil, lecithin, sodium lactate, polyoxyethylene and polypropylene fatty acid ester, sorbitan fatty acid ester, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulphate, zinc sulphate, calcium sulphate, potash, calcium phosphate, dicalcium phosphate, potassium bromide, potassium iodide, talcum, kaolin, pectin, crosspovidone, agar and bentonite.

Pharmaceutical formulations or dosage forms in the form of tablets, effervescent tablets, chewing tablets, dragees, capsules, drops, juices or syrups are, for example, suitable for oral administration. Oral pharmaceutical formulations may also be in the form of multiparticulates such as granules, pellets, spheres, crystals and the like, optionally compressed into a tablet, filled into a capsule, filled into a sachet or suspended in a suitable liquid medium. Oral pharmaceutical formulations may also be provided with an enteric coating.

Pharmaceutical formulations that are suitable for parenteral, topical and inhalative administration include but are not limited to solutions, suspensions, easily reconstitutable dry preparations and sprays.

Suppositories are a suitable pharmaceutical formulation for rectal administration. Formulations in a deposit, in dissolved form, for example, in a patch optionally with the addition of agents to promote skin penetration, are examples of suitable formulations for percutaneous administration.

One or both of the components (a) and (b) may be present in the pharmaceutical formulation according to the invention at least partially in controlled-release form. Moreover, any controlled release/immediate release combination of the components may also be present in the pharmaceutical formulation of the invention. For example, one or both of the components may be released from the formulations of the invention with a certain delay, e.g. if administered orally, rectally or percutaneously. Such formulations are particularly useful for "once-daily" or "twice-daily" preparations, which only have to be taken once a day, respectively, twice a day. Suitable controlled-release materials are well known to persons skilled in the art.

The pharmaceutical formulations of the invention may be produced using materials, means, devices and processes that are well known in the prior art of pharmaceutical formulations, as described for example in "Remington's Pharmaceutical Sciences", A. R. Gennaro (ed.), 17$^{th}$ edition, Mack Publishing Company, Easton, Pa. (1985), in particular in part 8, chapters 76 to 93.

In order to obtain a solid pharmaceutical formulation such as a tablet, for example, the components of the pharmaceutical composition may be granulated with a pharmaceutical carrier, for example conventional tablet ingredients such as corn starch, lactose, saccharose, sorbitol, talcum, magnesium stearate, dicalcium phosphate or pharmaceutically acceptable gums, and pharmaceutical diluents, for example water, in order to form a solid composition that contains the components in homogeneous distribution. The term "homogeneous distribution" is taken to mean that the components are distributed uniformly over the entire composition, so that said composition may easily be divided into equally effective unit dose forms, such as tablets, pills or capsules and the like. The solid composition is then divided into unit dose forms. The tablets or pills of the pharmaceutical composition according to the invention may also be coated or compounded in a different manner, in order to provide a dose form with a controlled release.

If one of the components is to be released prior to the other component, for example at least 30 minutes or 1 hour beforehand, pharmaceutical formulations having a corresponding release profile may be prepared. An example of such a formulation is an osmotically driven release system for achieving a delayed release of one component via a coating that itself contains the other component which is accordingly released earlier. In a release system of this kind, which is particularly suitable for oral administration, at least part, and preferably all, of the surface of the release system, preferably those parts that will come into contact with the release medium, is/are semipermeable, preferably equipped with a semipermeable coating, so the surface(s) is/are permeable to the release medium, but substantially, preferably entirely, impermeable to the active ingredient, the surface(s) and/or optionally the coating comprising at least one opening for releasing the active ingredient. Moreover, precisely that/those surface(s) that is/are in contact with the release medium is/are provided with a coating containing and releasing the other component. This is preferably taken to mean a system in tablet form comprising a release opening, an osmotic pharmaceutical composition core, a semipermeable membrane and a polymer portion that exerts pressure upon swelling. A suitable example of this kind of system is the system distributed by ALZA Corporation, USA under the tradenames OROS®, in particular, the OROS® Push-Pull™ System, the OROS® Delayed Push-Pull™ System, the OROS® Multi-Layer Push-Pull™ system, the OROS® Push-Stick System and also, in specific cases, the L-OROS™. Embodiments and examples of osmotically driven release systems are disclosed, for example, in U.S. Pat. Nos. 4,765,989, 4,783,337 and 4,612,008, the entire disclosures of each of which are incorporated herein by reference.

A further example of a suitable pharmaceutical formulation is a gel-matrix tablet, such as the products developed by Penwest Pharmaceuticals (for example, under TimeRX). Suitable examples are provided in U.S. Pat. Nos. 5,330,761, 5,399,362, 5,472,711 and 5,455,046, the entire disclosures of each of which are incorporated herein by reference. Particularly suitable is a retarding matrix formulation, with an inhomogeneous distribution of the pharmaceutically active composition, whereby, for example, one component can be distributed in the outer region (the portion that comes into contact with the release medium most quickly) of the matrix and the other component is distributed inside the matrix. On contact with the release medium, the outer matrix layer initially (and rapidly) swells and initially releases the first component, followed by the significantly (more) retarded release of the other component. Examples of a suitable matrix include matrices with 1 to 80% by weight of one or more hydrophilic or hydrophobic polymers as pharmaceutically acceptable matrix formers. A further example of a suitable matrix may be inferred from U.S. Pat. No. 4,389,393, the entire disclosure of which is incorporated herein by reference.

The amount of the pharmaceutically active combination according to the invention to be administered to the patient may vary depending on different factors well known to those skilled in the art, for example, the weight of the patient, the route of administration, or the severity of the illness.

In another one of its aspects the present invention relates to a combination as described herein for the treatment of pain, wherein the pain is preferably selected from the group consisting of inflammatory pain, neuropathic pain, acute pain, chronic pain, visceral pain, migraine pain and cancer pain.

In a further aspect, the present invention relates to the use of a pharmaceutical combination of the invention as described herein for the treatment of pain, said pain preferably including, but not being limited to, inflammatory pain, neuropathic pain, acute pain, chronic pain, visceral pain, migraine pain and cancer pain.

In another aspect, the present invention relates to the use of a pharmaceutical combination of the invention as described herein for the preparation of a medicament for the treatment of pain, said pain preferably including, but not being limited to, inflammatory pain, neuropathic pain, acute pain, chronic pain, visceral pain, migraine pain and cancer pain.

In another aspect, the present invention relates to a method of treating pain in a mammal, preferably a human, which comprises administering an effective amount of an pharmaceutical combination of the invention as described herein to the mammal.

The present invention also relates to a kit comprising a combination or dosage forms comprising a combination or individual components of the combination.

Pharmacological Methods:

Randall-Selitto Test in Rats

The weight ratios of the components (a) and (b) that will lead to a supra-additive effect (synergistic effect) of the pharmaceutical composition of the invention may be determined via the test of Randall and Selitto as described in *Arch. Int. Pharmacodyn.*, 1957, 111: 409 to 419, which is a test of mechanical nociception that may be adapted to evaluate mechanical hyperanalgesia in models of inflammatory or neuropathic pain. The respective part of the literature is hereby incorporated by reference and forms part of the present disclosure.

Acute inflammation is induced by an intraplantar injection of 0.1 ml of a carrageenan-solution (0.5% in distilled water) into a hind paw of a rat. The mechanical nociceptive threshold is measured 4 hours later using an Algesiometer (Ugo Basile, Italy). The device generates a mechanical force with a linear increase over time. The force is applied to the dorsal surface of the inflamed rat hind paw via a cone-shaped stylus with a rounded tip (2 mm tip diameter). The nociceptive threshold is defined as the force (in grams) at which the rat vocalises (cut-off force 250 g). The mechanical nociceptive threshold is measured at different timepoints after the drug or vehicle administration. The antinociceptive and/or antihyperalgesic activity of the tested substance is expressed as percentages of maximum possible effect (% MPE). The group size is n=12.

The analysis of the results with respect to a supra-additive effect of the pharmaceutical composition of the invention comprising the components (a) and (b) is carried out via statistical comparison of the theoretical additive $ED_{50}$-value with the experimentally determined $ED_{50}$-value of a so-called fixed ratio combination (isobolographic analysis according to Tallarida J T, Porreca F, and Cowan A. Statistical analysis of drug-drug and site-site interactions with isobolograms. *Life Sci* 1989; 45: 947-961).

The interactions studies presented herein were performed using equieffective doses of the two components, calculated from the ratio of the respective $ED_{50}$ values of the components if administered alone.

The route of administration was intravenous (i.v.) for (1R,2R)-3-(3-dimethylamino-1-ethyl-2-methyl-propyl)-phenol hydrochloride (hereinafter referred to as tapentadol hydrochloride) and intraperitoneal (i.p.) for ketamine ((R, S)-ketamine hydrochloride) and memantine (memantine hydrochloride). When tapentadol hydrochloride was applied alone, the peak effect was reached 15 min p. appl. (timepoint of first measurement) and an $ED_{50}$-value of 1.75 (1.69-1.81) mg/kg i.v. was calculated. Ketamine hydrochloride induced a dose-dependent analgesic effect with an $ED_{50}$-value of 20.2 (19.0-21.3) mg/kg i. p. respectively, reaching the peak effect 15 min p. appl. According to their respective timepoint of peak effect, (1R,2R)-3-(3-dimethylamino-1-ethyl-2-methyl-propyl)-phenol hydrochloride was applied 15 min and ketamine hydrochloride 15 min before timepoint of measurement of the interaction-experiments (both components were applied simultaneously). Memantine hydrochloride induced a dose-dependent analgesic effect with an $ED_{50}$-value of 19.1 (17.0-22.0) mg/kg i. p. respectively, reaching the peak effect 15 min p. appl. According to their respective timepoint of peak effect, (1R,2R)-3-(3-dimethyl-amino-1-ethyl-2-methyl-propyl)-phenol hydrochloride was applied 15 min and memantine hydrochloride 15 min before timepoint of measurement of the interaction-experiments (both components were applied simultaneously).

Thus, the time point of $ED_{50}$ calculation of both combinations corresponded to the timepoint of the peak effect of the respective compound. The isobolographic analysis revealed that the experimental $ED_{50}$-values of the combinations were significantly lower than the respective theoretical $ED_{50}$-values. Thus, the combination studies demonstrated significant synergistic interaction of (1R,2R)-3-(3-dimethylamino-1-ethyl-2-methyl-propyl)-phenol hydrochloride with the NMDA-antagonists, ketamine hydrochloride and memantine hydrochloride.

The results of the isobolographic analysis are summarized in the following table. Experimental $ED_{50}$ values of tapentadol hydrochloride (A) and ketamine hydrochloride or A and memantine hydrochloride, respectively, and isobolographic analysis of the interaction between A and these NMDA-antagonists:

| Substance/ $ED_{50}$ [mg/kg] | tapentadol hydro-chloride (A) | ketamine hydro-chloride | memantine hydro-chloride | Theoretical $ED_{50}$ of the combination | Experimental $ED_{50}$ of the combination | Interaction |
|---|---|---|---|---|---|---|
| tapentadol hydrochloride (A) + ketamine hydrochloride | 1.75 (1.69-1.81) | 20.2 (19.0-21.3) | — | 11.0 (10.6-11.3) | 9.2 (8.6-9.7) | supra-additive (p < 0.001) |
| tapentadol hydrochloride (A) + memantine hydrochloride | 1.75 (1.69-1.81) | — | 19.1 (17.0-22.0) | 10.4 (9.7-11.1) | 9.6 (9.0-10.2) | supra-additive (p < 0.05) | p: Level of statistical significance

The dose ratio of A to ketamine hydrochloride can be calculated to be 1:11.5 and the dose ratio of A to memantine hydrochloride can be calculated to be 1:10.9.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A pharmaceutical combination comprising as components:
 (a) at least one stereoisomer of 3-(3-dimethylamino-1-ethyl-2-methyl-propyl)-phenol compound of formula (I),

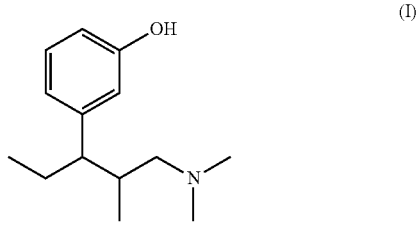 [SMILES: CCC(c1cccc(O)c1)C(C)CN(C)C]

or a pharmaceutically acceptable acid addition salt thereof, and
 (b) at least one NMDA-antagonist selected from the group consisting of (R,S)-ketamine, (S)-ketamine, and memantine.

2. The combination according to claim 1, wherein the compound of formula (I) or pharmaceutically acceptable acid addition salt thereof is selected from the group consisting of:
 (1R,2R)-3-(3-dimethylamino-1-ethyl-2-methyl-propyl)-phenol or a pharmaceutically acceptable acid addition salt thereof,
 (1S,2S)-3-(3-dimethylamino-1-ethyl-2-methyl-propyl)-phenol or a pharmaceutically acceptable acid addition salt thereof,
 (1R,2 S)-3-(3-dimethylamino-1-ethyl-2-methyl-propyl)-phenol or a pharmaceutically acceptable acid addition salt thereof,
 (1 S,2R)-3-(3-dimethylamino-1-ethyl-2-methyl-propyl)-phenol or a pharmaceutically acceptable acid addition salt thereof, and
 mixtures of two or more thereof in any mixing ratio.

3. The combination according to claim 2, wherein the compound of formula (I) or pharmaceutically acceptable acid addition salt thereof is selected from the group consisting of:
 (1R,2R)-3-(3-dimethylamino-1-ethyl-2-methyl-propyl)-phenol or a pharmaceutically acceptable acid addition salt thereof,
 (1S,2S)-3-(3-dimethylamino-1-ethyl-2-methyl-propyl)-phenol or a pharmaceutically acceptable acid addition salt thereof, and
 mixtures thereof in any mixing ratio.

4. The combination according to claim 3, wherein the compound of formula (I) is (1R,2R)-3-(3-dimethylamino-1-ethyl-2-methyl-propyl)-phenol of formula (I'):

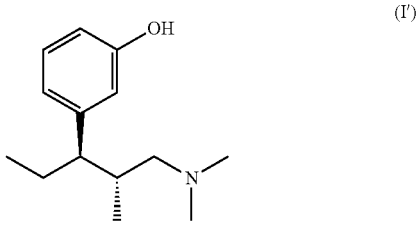 [SMILES: CC[C@@H](c1cccc(O)c1)[C@@H](C)CN(C)C]

or a pharmaceutically acceptable acid addition salt thereof.

5. The combination according to claim 4, wherein the compound of formula (I') is the hydrochloride acid addition salt of (1R,2R)-3-(3-dimethylamino-1-ethyl-2-methyl-propyl)-phenol.

6. A pharmaceutical dosage form comprising a combination according to claim 1 and at least one pharmaceutically acceptable auxiliary agent.

7. A dosage form according to claim 6, wherein said dosage form is suitable for oral, intravenous, intraarterial, intraperitoneal, intradermal, transdermal, intrathekal, intramuscular, intranasal, transmucosal, subcutaneous, or rectal administration.

8. A dosage form according to claim 6, wherein at least one of the components (a) and (b) is present in controlled-release form.

9. A method of treating pain in a mammal in need thereof, said method comprising administering to said mammal a pharmacologically effective amount of a combination according to claim 1.

10. The method according to claim 9, wherein the pain is selected from the group consisting of inflammatory pain, neuropathic pain, acute pain, chronic pain, visceral pain, migraine pain and cancer pain.

11. The method according to claim 9, wherein the pain is inflammatory pain.

12. The method according to claim 9, wherein component (a) and component (b) of the combination are administered simultaneously to the mammal.

13. The method according to claim 9, wherein component (a) and component (b) of the combination are administered or sequentially to the mammal in either order.

14. The method according to claim 9, wherein component (a) and component (b) of the combination are administered via different pathways of administration.

15. The method according to claim 9, wherein component (a) and component (b) of the combination are administered via the same pathway of administration.

16. A pharmaceutical combination comprising as components:
 (a) the compound (1R,2R)-3-(3-dimethylamino-1-ethyl-2-methyl-propyl)-phenol of formula (I'):

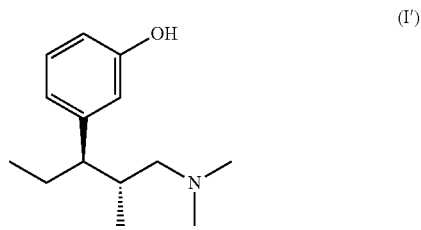 [SMILES: CC[C@@H](c1cccc(O)c1)[C@@H](C)CN(C)C]

or a pharmaceutically acceptable acid addition salt thereof; and
 (b) at least one NMDA-antagonist selected from the group consisting of (R,S)-ketamine, (S)-ketamine, and memantine.

* * * * *